United States Patent
Nishizaki et al.

(10) Patent No.: US 9,603,821 B2
(45) Date of Patent: Mar. 28, 2017

(54) INHIBITOR OF τ PROTEIN PHOSPHORYLATION

(71) Applicant: NISHIZAKI BIOINFORMATION RESEARCH INSTITUTE, Kobe-shi, Hyogo (JP)

(72) Inventors: Tomoyuki Nishizaki, Kobe (JP); Akito Tanaka, Toyonaka (JP)

(73) Assignee: Nishizaki Bioinformation Research Institute, Kobe (JP)

( * ) Notice: Subject to any disclaimer, the term of this patent is extended or adjusted under 35 U.S.C. 154(b) by 0 days.

(21) Appl. No.: 14/769,707

(22) PCT Filed: Feb. 21, 2014

(86) PCT No.: PCT/JP2014/054231
§ 371 (c)(1),
(2) Date: Aug. 21, 2015

(87) PCT Pub. No.: WO2014/129598
PCT Pub. Date: Aug. 28, 2014

(65) Prior Publication Data
US 2016/0008308 A1 Jan. 14, 2016

(30) Foreign Application Priority Data
Feb. 22, 2013 (JP) ................................. 2013-033668

(51) Int. Cl.
*A61K 31/20* (2006.01)
(52) U.S. Cl.
CPC .................................. *A61K 31/20* (2013.01)

(58) Field of Classification Search
CPC ...................................................... A61K 31/20
See application file for complete search history.

(56) References Cited

U.S. PATENT DOCUMENTS

| 7,468,389 B2 | 12/2008 | Nishizaki et al. |
| 2005/0075393 A1 | 4/2005 | Nishizaki et al. |
| 2013/0331454 A1* | 12/2013 | Nishizaki ............... C07C 53/132 514/572 |

FOREIGN PATENT DOCUMENTS

| JP | 2008-143819 A | 6/2008 | |
| JP | 2010-202525 A | 9/2010 | |
| WO | WO 02/50013 A1 | 6/2002 | |
| WO | WO 2012/067111 | * 5/2012 | ........... C07C 53/132 |

OTHER PUBLICATIONS

Good, N. et al., Differential regulations of glycogen synthase kinase-3beta by protein kinase C isotypes, 1992, The Journal of Biological Chemistry, vol. 267, No. 24, pp. 16878-16882.*

(Continued)

*Primary Examiner* — Yate K Cutliff
(74) *Attorney, Agent, or Firm* — Leydig, Voit & Mayer, Ltd.

(57) ABSTRACT

8-[2-(2-pentyl-cyclopropylmethyl)-cyclopropyl]-octanoic acid has a protein tyrosine phosphatase 1B (PTP1B) inhibitory action, an Akt activating action, a GSK-3β phosphorylation promoting action, and a suppressive action on τ protein phosphorylation induced by $A\beta_{1-42}$, and is useful as a therapeutic drug for Alzheimer-type dementia, an antidepressant and/or an anti-aging drug.

2 Claims, 7 Drawing Sheets

(56) References Cited

OTHER PUBLICATIONS

Scheid, M.P. et al., Unravelling the activation mechanisms of protein kinase B/Akt, 2003, FEBS Letters, 546, pp. 108-112.*
Song, G. et al., The activation fo Akt/PKB signaling pathway and cell survival, 2005, J. Cell. MOl. Med. vol. 9, No. 1, pp. 59-71.*
Forlenza et al., *Journal of Neural Transmission*, 107(10): 1201-1212 (2000).
Isagawa et al., *Biochemical and Biophysical Research Communications*, 273(1): 209-212 (2000).
Kanno et al., *Journal of Neurochemistry*, 95(3): 695-702 (2005).
Kanno et al., *Biochem. J.*, 450(2): 303-309 (2013).
Kanno et al., *Journal of Cellular Physiology*, 221(1): 183-188 (2009).
Kanno et al., *Cellular Physiology and Biochemistry*, 30(1): 75-82 (2012).
Kanno et al., *Journal of Lipid Research*, 47(6): 1146-1156 (2006).
Kanno et al., *Lipids*, 47(7): 687-695 (2012).
Nagata et al., *Behavioural Brain Research*, 206(1): 151-154 (2010).
Nagata et al., *Psychogeriatrics*, 5: 122-126 (2005).
Nishizaki et al., *Personalized Medicine Universe*, 3: 28-34 (2014).
Shimizu et al., *Cellular Physiology and Biochemistry*, 27(2): 149-158 (2011).
Sun et al., *Drug Development Research*, 65(3): 156-169 (2005).
Tanaka et al., *Bioorganic & Medicinal Chemistry Letters*, 13(6): 1037-1040 (2003).
Tsuchiya et al., *Cellular Physiology and Biochemistry*, 33(4): 1097-1105 (2014).
Xu et al., *Acta Biochemica et Biophysica Sinca*, 37(5): 349-354 (2005).
Yaguchi et al., *Neurochem. Res.*, 35(5): 712-717 (2010).
Yaguchi et al., *NeuroReport*, 17(1): 105-108 (2006).
Yamamoto et al., *Neuroscience*, 130(1): 207-213 (2005).
Hongpaisan et al., "PKC $\epsilon$ Activation Prevents Synaptic Loss, A$\beta$ Elevation, and Cognitive Deficits in Alzheimer's Disease Transgenic Mice," *The Journal of Neuroscience*, 31(2): 630-643 (2011).
Sun et al., "Protein Kinase C Activators as Synaptogenic and Memory Therapeutics," *Arch. Pharm. Chem. Life Sci.*, 342(12): 689-698 (2009).
European Patent Office, Supplementary European Search Report in European Patent Application No. 14754043 (Jul. 19, 2016).
Forlenza et al., "Muscarinic agonists reduce tau phosphorylation in non-neuronal cells via GSK-3$\beta$ inhibition and in neurons," *Journal of Neural Transmission*, 107(10): 1201-1212 (2000).
Isagawa et al., "Dual Effects of PKN$\alpha$ and Protein Kinase C on Phosphorylation of Tau Protein by Glycogen Synthase Kinase-3$\beta$," *Biochemical and Biophysical Research Communications*, 273(1): 209-212 (2000).
Kanno et al., "8-[2-(2-pentyl-cyclopropylmethyl)-cyclopropyl]-octanoic acid stimulates GABA release from interneurons projecting to CA1 pyramidal neurons in the rat hippocampus via presynaptic $\alpha$7 acetylcholine receptors," *Journal of Neurochemistry*, 95(3): 695-702 (2005).
Kanno et al., "The linoleic acid derivative DCP-LA increases membrane surface localization of the $\alpha$7 ACh receptor in a protein 4.1N-dependent manner," *Biochem. J.*, 450(2): 303-309 (2013).
Kanno et al., "DCP-LA Stimulates AMPA Receptor Exocytosis Through CaMKII Activation due to PP-1 Inhibition," *Journal of Cellular Physiology*, 221(1): 183-188 (2009).
Kanno et al., "Linoleic Acid Derivative DCP-LA Stimulates Vesicular Transport of $\alpha$7 ACh Receptors Towards Surface Membrane," *Cellular Physiology and Biochemistry*, 30(1): 75-82 (2012).
Kanno et al., "The linoleic acid derivative DCP-LA selectively activates PKC-$\epsilon$, possibly binding to the phosphatidylserine binding site," *Journal of Lipid Research*, 47(6): 1146-1156 (2006).
Kanno et al., "8-[2-(2-Pentyl-Cyclopropylmethyl)-Cyclopropyl]-Octanoic Acid and Its Diastereomers Improve Age-Related Cognitive Deterioration," *Lipids*, 47(7): 687-695 (2012).
Nagata et al., "DCP-LA neutralizes mutant amyloid $\beta$ peptide-induced impairment of long-term potentiation and spatial learning," *Behavioural Brain Research*, 206(1): 151-154 (2010).
Nagata et al., "The newly synthesized linoleic acid derivative DCP-LA ameliorates memory deficits in animal models treated with amyloid-$\beta$ peptide and scopolamine," *Psychogeriatrics*, 5: 122-126 (2005).
Nishizaki et al., "Evaluation of the newly synthesized linoleic acid derivative DCP-LA as a potential anti-dementia drug," *Personalized Medicine Universe*, 3: 28-34 (2014).
Shimizu et al., "$\alpha,\beta$-DCP-LA Selectively Activates PKC-$\epsilon$ and Stimulates Neurotransmitter Release with the Highest Potency among 4 Diastereomers," *Cellular Physiology and Biochemistry*, 27(2): 149-158 (2011).
Sun et al., "Protein Kinase C Substrate Activators: Potential as Novel Antidepressants," *Drug Development Research*, 65(3): 156-169 (2005).
Tanaka et al., "The Newly Synthesized Linoleic Acid Derivative FR236924 Induces a Long-Lasting Facilitation of Hippocampal Neurotransmission by Targeting Nicotinic Acetylcholine Receptors," *Bioorganic & Medicinal Chemistry Letters*, 13(6): 1037-1040 (2003).
Tsuchiya et al., "PTP1B Inhibition Causes Rac1 Activation by Enhancing Receptor Tyrosine Kinase Signaling," *Cellular Physiology and Biochemistry*, 33(4): 1097-1105 (2014).
Xu et al., "Prolonged Alzheimer-like Tau Hyperphosphorylation Induced by Simultaneous Inhibition of Phosphoinositol-3 Kinase and Protein Kinase C in N2a cells," *Acta Biochemica et Biophysica Sinca*, 37(5): 349-354 (2005).
Yaguchi et al., "Linoleic Acid Derivative DCP-LA Protects Neurons from Oxidative Stress-Induced Apoptosis by Inhibiting Caspase-3/-9 Activation," *Neurochem. Res.*, 35(5): 712-717 (2010).
Yaguchi et al., "Linoleic acid derivative DCP-LA improves learning impairment in SAMP8," *NeuroReport*, 17(1): 105-108 (2006).
Yamamoto et al., "The linoleic acid derivative FR236924 facilitates hippocampal synaptic transmission by enhancing activity of presynaptic $\alpha$7 acetylcholine receptors on the glutamatergic terminals," *Neuroscience*, 130(1): 207-213 (2005).

* cited by examiner

INHIBITOR OF τ PROTEIN PHOSPHORYLATION

CROSS-REFERENCE TO RELATED APPLICATIONS

This patent application is the U.S. national phase of International Patent Application No. PCT/JP2014/054231, filed Feb. 21, 2014, which claims the benefit of Japanese Patent Application No. 2013-033668, filed on Feb. 22, 2013, which are incorporated by reference in their entireties herein.

TECHNICAL FIELD

The present invention relates to a novel use of 8-[2-(2-pentyl-cyclopropylmethyl)-cyclopropyl]-octanoic acid (DCP-LA), more particularly, use of DCP-LA as a protein tyrosine phosphatase 1B inhibitor, an Akt activator, a GSK-3β phosphorylation promoter or a τ protein phosphorylation inhibitor.

BACKGROUND ART

In recent years, dementia has become a significant medical problem worldwide. Dementia is a disease associated with various symptoms mainly including learning and memory disorders and impaired judgment, in which the symptoms and progression thereof vary depending on the causative diseases thereof. In any case, they are common in that they markedly impair the quality of life of the patients. In consideration of the fact that dementia forces huge labor to the caregivers including patients' families, it is a very serious social problem. It is predicted that the dementia patients will further increase hereafter in Japan, since an increase in the population of elderly people due to prolongation of life span is related to an increase in the dementia patients. In addition, there are many people suffering from cognitive impairment due to aging, which is not classified as dementia.

Various compounds capable of improving dementia have been reported. 8-[2-(2-Pentyl-cyclopropylmethyl)-cyclopropyl]-octanoic acid (DCP-LA), which is a linoleic acid derivative, is a compound having a long-term enhancing action on synapse transmission efficiency, which can delay metabolism in the body and can maintain stable LTP (long-term potentiation)-like enhancement of synapse transmission (patent document 1). LTP is considered to be involved in the improvement of, for example, various neurological and mental diseases such as Alzheimer's disease and the like, and therefore, a substance that induces LTP expression has a possibility of providing a therapeutic or prophylactic drug for these neurological and mental diseases including dementia.

Some reports have also been documented as regards DCP-LA. For example, it has been reported that DCP-LA activates PKC-ε selectively and directly (non-patent document 1), DCP-LA improves cognitive dysfunction of senescence accelerated mouse (non-patent document 2), DCP-LA increases release of γ aminobutyric acid from hippocampus nerve cells (non-patent document 3), DCP-LA improves cognitive dysfunction of amyloid β peptide or scopolamine-treated rat (non-patent document 4), and DCP-LA promotes hippocampal synaptic transmission with α7 nicotinic acetylcholine receptor expressed in glutamatergic presynaptic cell as a target (non-patent document 5). Furthermore, it has been reported in recent years that DCP-LA has an action to suppress nerve cell death induced by oxidative stress (patent document 2).

However, a detailed mechanism of the synaptic transmission promoting action of DCP-LA has not been elucidated yet. Elucidation of the mechanism to clarify the point of action of DCP-LA leads to the development of a prophylactic or therapeutic drug for various neurodegenerative diseases including Alzheimer's disease, which has an action mechanism different from that of existing drugs.

DOCUMENT LIST

Patent Documents patent document 1: WO02/50013
patent document 2: JP-A-2008-143819

Non-Patent Documents non-patent document 1: Kanno T et al., J Lipid Res., 2006, 47(6):1146-56.
non-patent document 2: Yaguchi T et al., Neuroreport, 2006, 23; 17(1):105-8.
non-patent document 3: Kanno T et al., J Neurochem., 2005, 95(3):695-702.
non-patent document 4: Nagata T et al., Psychogeriatrics, 2005, 5:122-126.
non-patent document 5: Yamamoto et al., Neuroscience 2005, 130(1):207-213.

SUMMARY OF THE INVENTION

Problems to be Solved by the Invention

The present invention aims to elucidate the pharmacological action of DCP-LA and an influence thereof on living organisms, and provide a novel use.

Means of Solving the Problems

The present inventors have conducted intensive studies in an attempt to obtain a medicine capable of more effectively improving the cognitive function. Surprisingly, they have found that DCP-LA also has, besides an LTP-like potentiating action, various pharmacological actions useful for the improvement of cognitive function, which resulted in the completion of the present invention. Therefore, the present invention is as described below.

[1] A protein tyrosine phosphatase 1B (PTP1B) inhibitor comprising DCP-LA as an active ingredient.
[2] An Akt activator comprising DCP-LA as an active ingredient.
[3] A GSK-3β phosphorylation promoter comprising DCP-LA as an active ingredient.
[4] A τ protein phosphorylation inhibitor comprising DCP-LA as an active ingredient.
[5] A therapeutic drug for Alzheimer-type dementia, comprising the agent of any of the above-mentioned [1]-[4].
[6] An antidepressant, comprising the agent of any of the above-mentioned [1]-[4].
[7] An anti-aging drug, comprising the agent of any of the above-mentioned [1]-[4].
[8] The agent of any of the above-mentioned [1]-[4], which is a reagent for study.
[9] A method of inhibiting PTP1B, comprising treating cells with DCP-LA.

[10] A method of activating Akt, comprising treating cells with DCP-LA.
[11] A method of activating GSK-3β phosphorylation, comprising treating cells with DCP-LA.
[12] A method of suppressing τ protein phosphorylation, comprising treating cells with DCP-LA.
[13] A method for the prophylaxis or treatment of Alzheimer-type dementia or depression, comprising inhibiting PTP1B by administering an effective amount of DCP-LA to a patient in need thereof.
[14] A method for the prophylaxis or treatment of Alzheimer-type dementia or depression, comprising activating Akt activity by administering an effective amount of DCP-LA to a patient in need thereof.
[15] A method for the prophylaxis or treatment of Alzheimer-type dementia or depression, comprising activating GSK-3β phosphorylation by administering an effective amount of DCP-LA to a patient in need thereof.
[16] A method for the prophylaxis or treatment of Alzheimer-type dementia or depression, comprising suppressing τ protein phosphorylation by administering an effective amount of DCP-LA to a patient in need thereof.

Effect of the Invention

DCP-LA has pharmacological actions superior in the improvement of cognitive function (protein tyrosine phosphatase 1B (PTP1B) inhibitory action, Akt activating action, GSK-3β phosphorylation promoting action and τ protein phosphorylation suppressive action), and is also useful as various reagents based on such actions, a therapeutic drug for Alzheimer-type dementia, an antidepressant or an anti-aging drug. Since the agent of the present invention has an action mechanism different from that of existing drugs, it can avoid side effects posing problems in existing drugs. In addition, the agent of the present invention can be used as a reagent for study and can be a useful tool for the development of such prophylactic or therapeutic drugs.

BRIEF DESCRIPTION OF THE DRAWINGS

FIG. 3 is a graph showing induction of Akt activation by DCP-LA. A hippocampus section of rat was not treated or treated for 3 min with DCP-LA (100 nM), and subjected to Western blotting using antibodies against phospho-threonine 308 AKT (P-T308), phospho-serine 473 Akt (P-S473) and Akt. The signal intensity of P-T308 or P-S473 was normalized against the signal intensity of Akt. In the graph, each column shows mean (±SEM) proportion of phosphorylated Akt relative to the total Akt (n=4 in each experiment). P value, unpaired t-test.
FIG. 4 is a graph showing promotion of GSK-3β phosphorylation by DCP-LA. A hippocampus section of rat was not treated or treated for 3 min with DCP-LA (100 nM), and subjected to Western blotting using antibodies against phospho-serine 9 GSK-3β (P-Ser9-GSK-3β) and GSK-3β. The signal intensity of P-Ser9-GSK-3β was normalized against the signal intensity of GSK-3β. In the graph, each column shows mean (±SEM) proportion of Ser9 phosphorylated GSK-3β relative to the total GSK-3β (n=4 in each experiment). P value, unpaired t-test.
FIG. 5 is a graph showing that DCP-LA suppresses phosphorylation of τ protein induced by amyloid $β_{1-42}$ ($Aβ_{1-42}$) A hippocampus section of rat was treated with $Aβ_{1-42}$ (1 μM) for 3 hr in the presence or absence of DCP-LA (100 nM), and subjected to Western blotting using antibodies against phospho serine 202/threonine 205 τ protein (P-Ser202/Thr205-Tau) and τ protein. The signal intensity of P-Ser202/Thr205-Tau was normalized against the signal intensity of total τ protein. In the graph, each column shows mean (±SEM) proportion of Ser202/Thr205 phosphorylated τ protein relative to the total τ protein (n=4 in each experiment). P value, Dunnett's test.
FIG. 6 is a graph showing that DCP-LA improves spatial learning and memory disorders in 5XFAD mouse. DCP-LA (1 mg/kg), galanthamine (Galant) (2.5 mg/kg) or PEG30 was administered to the mouse 30 min before a water maze test. The water maze test was performed every day, and each drug was administered every day. (A,C) Each point shows mean (±SEM) acquisition latency of two consecutive days (n=11-12 in each experiment). ***$P<0.0001$, Fisher's PLSD (protected least significant difference test) NS, not significant. (B,D) Each column shows mean retention latency (n=11-12 in each experiment). P value, Dunnett's test. NS, not significant.
FIG. 7 is a graph showing phosphorylation of GSK-3β by PKCε activated by DCP-LA. GSK-3β was reacted with PKCε (1 μg/ml) under cell-free conditions in the presence or absence of DCP-LA and with or without addition of GF109203X (GF in graph) (100 nM). Thereafter, Western blotting was performed using antibodies against serine 9 phosphorylated GSK-3β (P-Ser9-GSK-3β) and GSK-3β. The signal intensity of P-Ser9-GSK-3β was normalized against the signal intensity of GSK-3β. In the graph, each column shows mean (±SEM) proportion of serine 9 phosphorylated GSK-3β signal intensity relative to non-phosphorylated GSK-3β signal intensity (n=4 in each experiment). P value, Dunnett's test.

DESCRIPTION OF EMBODIMENTS

The present invention is explained in detail in the following.
8-[2-(2-Pentyl-cyclopropylmethyl)-cyclopropyl]-octanoic acid (abbreviated as necessary as DCP-LA in the present specification) used in the present invention as an active ingredient has the following structural formula.

DCP-LA can be produced, for example, by the method shown in WO 02/50013. While DCP-LA has 4 optical isomers (α,α-DCP-LA, α,β-DCP-LA, β,α-DCP-LA, β,β-DCP-LA), all of such isomers and mixtures thereof are encompassed within the scope of the present invention. These isomers can be produced, for example, by the method shown in WO 2012/067111.

The DCP-LA in the present invention may also be used in the form of a salt thereof. Such salt is not particularly limited, and a salt acceptable as a medicine or food is preferable. Examples thereof include salts with inorganic base (e.g., alkali metal such as sodium, potassium and the like; alkaline earth metal such as calcium, magnesium and the like; aluminum, ammonium), organic base (e.g., trimethylamine, triethylamine, pyridine, picoline, ethanolamine, diethanolamine, triethanolamine, dicyclohexylamine, N,N-dibenzylethylenediamine), inorganic acid (e.g., hydrochloric acid, hydrobromic acid, nitric acid, sulfuric acid, phosphoric acid), organic acid (e.g., formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid), basic amino acid (e.g., arginine, lysine, ornithine) or acidic amino acid (e.g., aspartic acid, glutamic acid) and the like.

When used in the present specification, the test subject can be a mammal. Examples of such mammal include primates (e.g., human, monkey, chimpanzee), rodents (e.g., mouse, rat, guinea pig), pets (e.g., dog, cat, rabbit), working animals and domestic animals (e.g., bovine, horse, swine, sheep, goat), with preference given to human.

When used in the present specification, a target cell to be treated with DCP-LA is a cell derived from the above-mentioned mammal, preferably a brain nerve cell and nerve cell model cell lines such as PC-12 cell line (adrenal gland medulla-derived pheochromocytoma) and the like. As used herein, the "treatment" means contacting the above-mentioned cell with DCP-LA for a time necessary and sufficient. While the time varies depending on the desired effect and the kind of the cells to be used, it is generally 1 min-5 hr, preferably about 3-30 min. Conveniently, it is performed by cultivation in a culture medium containing DCP-LA.

DCP-LA has, as shown with data in the Examples, (1) protein tyrosine phosphatase 1B (PTP1B) inhibitory action, (2) Akt activating action, (3) GSK-3β phosphorylation promoting action, and (4) suppressive action on τ protein phosphorylation induced by amyloid β peptide 1-42 ($Aβ_{1-42}$). Having these superior pharmacological actions, the present invention is useful for the prophylaxis or treatment of diseases associated with cognitive impairment, and can be provided as a pharmaceutical product (hereinafter to be also referred to as the medicine of the present invention). Moreover, there is a report teaching that depression is improved by phosphorylation (i.e., inactivation) of GSK-3β (Mol Psychiatry 2011; 16: 1068-1070, PNAS 2008; 105: 1333-1338). Accordingly, DCP-LA that induces phosphorylation of GSK-3β is also useful as an antidepressant.

Examples of the disease or condition associated with cognitive impairment include, specifically, various diseases and condition including dementia (e.g., senile dementia, dementia caused by various diseases such as Alzheimer-type dementia (Alzheimer's disease), cerebrovascular dementia, posttraumaic dementia, dementia caused by brain tumor, dementia caused by chronic subdural hematoma, dementia caused by normal pressure brain hydrocephalus, postmeningitis dementia, Parkinson type dementia and the like), cognitive impairment no dementia (e.g., mild cognitive impairment (MCI)), learning or memory disorders (e.g., learning and memory disorders associated with developmental brain disorder) and the like. As used in the present specification, "prophylaxis" means prevention of exteriorization of cognitive impairment, learning•memory disorder and the like in test subjects free from such symptoms, and the "treatment" means mitigation, prevention of exacerbation or delay of cognitive impairment, learning•memory disorder and the like in test subjects showing such symptoms. The "improvement" in test subjects free from cognitive impairment, learning•memory disorder and the like means improvement of cognitive ability, and learning•memorizing ability, and that in test subjects showing cognitive impairment, learning•memory disorder and the like means mitigation of the symptoms, preferably mitigation of the symptoms to the level posing no difficulty in daily living.

Preferable examples of the applicable disease include Alzheimer's disease. In view of the above-mentioned properties, an effect as an anti-aging drug can also be expected.

The pharmacological actions of DCP-LA clarified in the present invention are as follows.

(1) PTP1B Inhibitory Action

Protein tyrosine phosphatase (PTP) 1B is a cytosolic tyrosine phosphatase that controls phosphorylation state of tyrosine kinase, thereby involved in the adjustment of tyrosine kinase. As the involvement of protein phosphorylation in the neural activity attracts attention in recent years, application of PTP1B inhibition to neurodegenerative diseases has been expected.

Examples of reports indicating the possibility of a PTP1B inhibitor for application to pharmaceutical use include the following.

1. He R et al. Small molecule tools for functional interrogation of protein tyrosine phosphatases. FEBS J 2013; 280: 731-750.
2. Popov D. Endoplasmic reticulum stress and the on site function of resident PTP1B. Biochem Biophys Res Commun 2012; 422: 535-538.
3. Mody N et al. Susceptibility to diet-induced obesity and glucose intolerance in the APP (SWE)/PSEN1 (A246E) mouse model of Alzheimer's disease is associated with increased brain levels of protein tyrosine phosphatase 1B (PTP1B) and retinol-binding protein 4 (RBP4), and basal phosphorylation of S6 ribosomal protein. Diabetologia 2011; 54: 2143-2151.

(2) Akt Activating Action

It is one kind of Akt (also to be referred to as protein kinase B) serine threonine phosphorylated enzyme, and activation thereof is considered to essentially require phosphorylation of two amino acids of threonine 308 group (Thr 308) and serine 473 group (Ser 473). Akt has a function to specifically phosphorylate intracellular protein serine or threonine residue, and is known as an anti-aging factor.

Examples of reports showing the possibility of Akt activator for application to pharmaceutical use include the following.

1. O'Neill C et al. Insulin and IGF-1 signalling: longevity, protein homoeostasis and Alzheimer's disease. Biochem Soc Trans 2012; 40: 721-727.
2. Wu M et al. Important roles of Akt/PKB signaling in the aging process. Front Biosci (Schol Ed) 2010; 2: 1169-1188.
3. Camins A et al. Potential mechanisms involved in the prevention of neurodegenerative diseases by lithium. CNS Neurosci Ther 2009; 15: 333-344.

(3) GSK-3β Phosphorylation Promoting Action
(4) Suppressive Action on τ Protein Phosphorylation Induced by Aβ$_{1-42}$ Glycogen synthase kinase-3β (GSK-3β) is known as an enzyme that adds a phosphate group to τ (Tau) protein. It is known that phosphorylated τ protein is polymerized and intracerebrally accumulated as neurofibril (neurofibrillary tangle) in patients with Alzheimer's disease. Such neurofibrillary tangle is observed not only in Alzheimer's disease but also in denaturation diseases such as progressive supranuclear palsy, corticobasal degeneration, familial frontotemporal dementia, boxer's encephalopathy and the like. In the region where neurofibrillary tangle is observed, nerve cell fall off occurs simultaneously, which is considered to be deeply involved in the cognitive impairment characteristic of Alzheimer's disease and the like. Neurofibrillary tangle occurs with aging, emerges in the 20's in an early case of human, and emerges in almost all humans by the age of 80. In addition, β amyloid deposition is known to promote and enlarge formation of neurofibrillary tangle.

For example, the following reports suggest possibility of GSK-3β phosphorylation promoter and τ protein phosphorylation suppressing agent for pharmaceutical use.
1. Braak H and Braak E. Staging of Alzheimer's disease related neurofibrillary changes. Neurobiol Aging 1995; 16: 271-278.
2. Braak H and Braak E. Development of Alzheimer-related neurofibrillary changes in the neocortex inversely recapitulates cortical myelogenesis. Acta Neuropathol 1996; 92: 197-201.
3. Braak H and Braak E. Frequency of stages of Alzheimer related lesions in different age categories. Neurobiol Aging 1997; 18: 351-357.
4. Beurel E, Song L, Jope R S. Inhibition of glycogen synthase kinase-3 is necessary for the rapid antidepressant effect of ketamine in mice. Mol Psychiatry 2011; 16: 1068-1070.
5. Beaulieu J M, Zhang X, Rodriguiz R M, Sotnikova T D, Cools N J, Wetsel W C, Gainetdinov R R, Caron M G. Role of GSK3 beta in behavioral abnormalities induced by serotonin deficiency. PNAS 2008; 105: 1333-1338.

While the daily dose of the medicine of the present invention varies depending on the age and condition of individual patients to be treated, 0.001-100 mg of DCP-LA per 1 kg body weight of human or animal for intravenous administration, 0.001-10 mg of the compound per 1 kg body weight of human or animal for intramuscular administration, and 0.01-100 mg of the compound per 1 kg body weight of human or animal for oral administration are generally administered for the prophylaxis and/or treatment of the above-mentioned diseases.

The medicine of the present invention can contain, besides DCP-LA which is the active ingredient, any additive, for example, a pharmaceutically acceptable carrier. Examples of the pharmaceutically acceptable carrier include, but are not limited to, excipients such as sucrose, starch, mannit, sorbit, lactose, glucose, cellulose, talc, calcium phosphate, calcium carbonate and the like, binders such as cellulose, methylcellulose, hydroxypropylcellulose, polypropylpyrrolidone, gelatin, gum arabic, polyethylene glycol, sucrose, starch and the like, disintegrants such as starch, carboxymethylcellulose, hydroxypropylstarch, sodium-glycol-starch, sodium hydrogen carbonate, calcium phosphate, calcium citrate and the like, lubricants such as magnesium stearate, aerosil, talc, sodium lauryl sulfate and the like, aromatic substances such as citric acid, menthol, glycyllysin-ammonium salt, glycine, orange powder and the like, preservatives such as sodium benzoate, sodium bisulfite, methylparaben, propylparaben and the like, stabilizers such as citric acid, sodium citrate, acetic acid and the like, suspensions such as methylcellulose, polyvinylpyrrolidone, aluminum stearate and the like, dispersing agents such as surfactant and the like, diluents such as water, saline, orange juice and the like, base waxes such as cacao butter, polyethylene glycol, kerosene and the like, and the like.

In one embodiment, the medicine of the present invention can be formulated as a preparation preferable for oral administration. Examples of the preparation preferable for oral administration include a liquid wherein an effective amount of a substance is dissolved in a diluent such as water and saline, a capsule, granule, powder or tablet containing an effective amount of a substance as a solid or granules, a suspension wherein an effective amount of a substance is suspended in a suitable dispersion medium, an emulsion wherein a solution of an effective amount of a substance is dispersed and emulsified in a suitable dispersion medium, and the like.

In another embodiment, the medicine of the present invention can be formulated as a preparation preferable for parenteral administration. Examples of the preparation preferable for parenteral administration (e.g., intravenous injection, subcutaneous injection, muscular injection, topical injection and the like) include aqueous and nonaqueous isotonic aseptic injection liquids, which may contain antioxidant, buffer, bacteriostatic, isotonicity agent and the like. In addition, examples thereof include aqueous and non-aqueous aseptic suspensions, which may contain suspension, solubilizer, thickener, stabilizer, preservative and the like. Unit dose or plural doses of the preparation can be filled in a container such as ampoule and vial. Moreover, the active ingredient and a pharmaceutically acceptable carrier can be freeze-dried and preserved in a form that can be dissolved or suspended in a suitable aseptic vehicle immediately before use.

DCP-LA can be provided as a food. As mentioned above, DCP-LA as an active ingredient has (1) a protein tyrosine phosphatase 1B (PTP1B) inhibitory action, (2) an Akt activating action, (3) a GSK-3β phosphorylation promoting action, and (4) suppressive action on τ protein phosphorylation induced by amyloid β peptide 1-42 (Aβ$_{1-42}$)-, on mammals (e.g., mouse, rat, hamster, rabbit, cat, dog, bovine, sheep, monkey, human and the like), and can be provided as a functional food effective for the prophylaxis or treatment of Alzheimer-type dementia and the prophylaxis or treatment of depression. In addition, it can be provided as a functional food expected to provide an anti-aging effect.

The "food" in the present invention means all foods and drinks other than pharmaceutical products and quasi-drugs. For example, it includes, but is not limited to, food for specified health uses, food with nutrient function claims, and what is called supplements.

The medicine of the present invention may be packed or filled individually by a unit ingestion amount or a divided amount thereof, or packed or filled comprehensively by many unit ingestion amounts or divided amounts thereof.

When the medicine of the present invention is provided as a single preparation, the unit ingestion amount of the medicine or a divided amount thereof is the unit ingestion amount of the whole phospholipid compound of the present invention or a divided amount thereof.

Examples of the pharmaceutical product or food wherein a unit ingestion amount or a divided amount thereof is packed or filled individually include general packages (e.g., PTP (press through packing) sheet, paper container, film (e.g., plastic film) container, glass container, plastic container) packed or filled with the unit ingestion amount or a divided amount thereof. The pharmaceutical products or foods that are individually packed or filled may be further combined and packed or filled in a single container (e.g., paper container, film (e.g., plastic film) container, glass container, plastic container). Examples of the pharmaceutical product or food wherein many unit ingestion amounts or a divided amount thereof are/is comprehensively packed or filled include those wherein many tablets or capsules are packed or filled in a single container (e.g., paper container, film (e.g., plastic film) container, glass container, plastic container) without distinction. The pharmaceutical product or food of the present invention may contain a unit ingestion amount or a divided amount thereof in a number sufficient for long-term ingestion. For example, a food can contain same in a number sufficient for ingestion for not less than 3 days, preferably not less than 7 days, 10 days, 14 days or 21 days, or 1 month, 2 months, or not less than 3 months.

The medicine of the present invention may contain, besides DCP-LA which is an essential active ingredient, and one or more other kinds of compounds capable of preventing or treating neurodegenerative disease.

Examples of other compound for the prophylaxis or treatment of neurodegenerative disease include polyphenol, coenzyme Q10, β-sitosterol, isoflavone, mevinic acids, vitamin C, vitamin E, flavonoids, terpenes, folic acid, vitamin B6, vitamin B12, sesquirpene lactone, urokinase, nattokinase, dilinoleoylphosphatidylethanolamine, propyl sulfide, apple pectin, acetic acid, EPA, and DHA.

Furthermore, as mentioned above, DCP-LA has (1) a protein tyrosine phosphatase 1B (PTP1B) inhibitory action, (2) an Akt activating action, (3) a GSK-3β phosphorylation promoting action, and (4) suppressive action on τ protein phosphorylation induced by amyloid β peptide 1-42 ($A\beta_{1-42}$), and therefore, it can also be provided as various reagents. Specific examples of the reagent include protein tyrosine phosphatase 1B (PTP1B) inhibitor, Akt activator, GSK-3β phosphorylation promoter and τ protein phosphorylation inhibitor. All reagents can be useful tools for developing a therapeutic drug for dementia, an antidepressant, or an anti-aging drug, which have a new action mechanism that is conventionally absent, show reduced side effects and/or provide more enhanced effects.

For example, it has been reported that compounds that phosphorylate GSK-3β and compounds that suppress phosphorylation of τ protein can be therapeutic drugs for Alzheimer-type dementia. DCP-LA can be used as a positive control when such therapeutic drugs are developed.

The contents disclosed in any publication cited in the present specification, including patents and patent applications, are hereby incorporated in their entireties by reference, to the extent that they have been disclosed herein.

While the present invention is explained in further detail in the following by referring to Examples, it is not limited by the following Examples and the like.

EXAMPLES

Example 1

Protein Tyrosine Phosphatase 1B (PTP1B) Inhibitory Action (Material and Method)
Assay of PTP1B Activity Under Cell-Free Conditions Protein tyrosine phosphatase was measured under cell-free conditions by a method partially modified from the methods described in previous reports (Baba Y, et al. J Am Chem Soc 2003; 125; 9740-9749; Rice R L, et al. Biochemistry 1997; 36: 15965-15974). Human PTP1B was cloned to a pGEX-6P-3 vector having a GST tag at the $NH_2$ terminus, and expressed in competent E. coli BL21 (DE3) suitable for transformation and protein expression. GST fusion PTP1B was affinity-purified using glutathione sepharose 4B (GE Healthcare Bio-Science KK, Tokyo, Japan). It was reacted with p-nitrophenylphosphate (p-NPP) (Sigma, St. Louis, Mo., USA) as a substrate and PTP1B activity was measured. The enzyme was pre-incubated in a reaction medium [50 mM HEPES, 1 mM EDTA, 50 mM NaCl, 1 mM dithiothreitol, pH 7.2] at 37° C. for 30 min in the presence or absence of DCP-LA at a given concentration (1-100 μM) and with or without addition of $Na_3VO_4$ which is a PTP1B inhibitor. Then, p-NPP (10 mM) was added to the reaction medium, and the mixture was incubated for 60 min. The reaction was discontinued by the addition of 0.1N NaOH. Dephosphorylated p-NPP, i.e., p-NP, was quantified at an absorbance of 405 nm by using SpectraMax PLUS384 (Molecular Devices, Sunnyvale, Calif., USA).

(Results)

Figure 1:
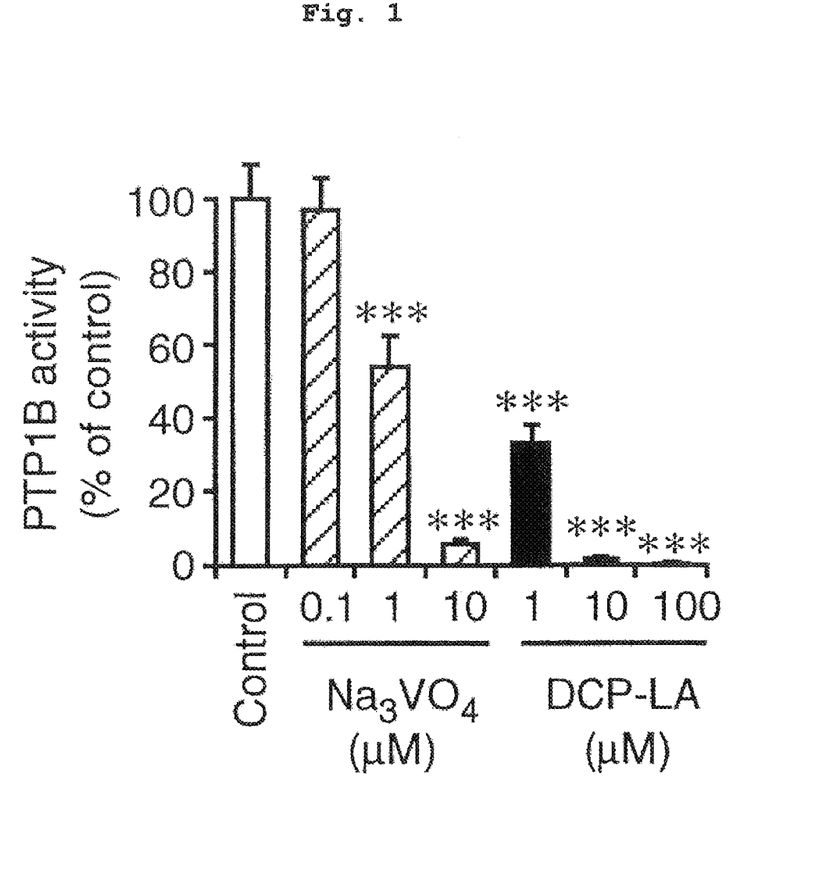
FIG. 1 is a graph showing induction of protein tyrosine phosphatase (PTP1B) inhibition by DCP-LA. PTP1B was reacted with p-NPP under cell-free conditions in the presence and absence of $Na_3VO_4$ (1-10 μM), and dephosphorylated p-NPP was quantified. In the graph, each column shows mean (±SD) percentage to the phosphatase activity to be the standard (control) (n=4 in each experiment). ***$P<0.0001$, Dunnett's test.

The results are shown in FIG. 1.

Figure 2:
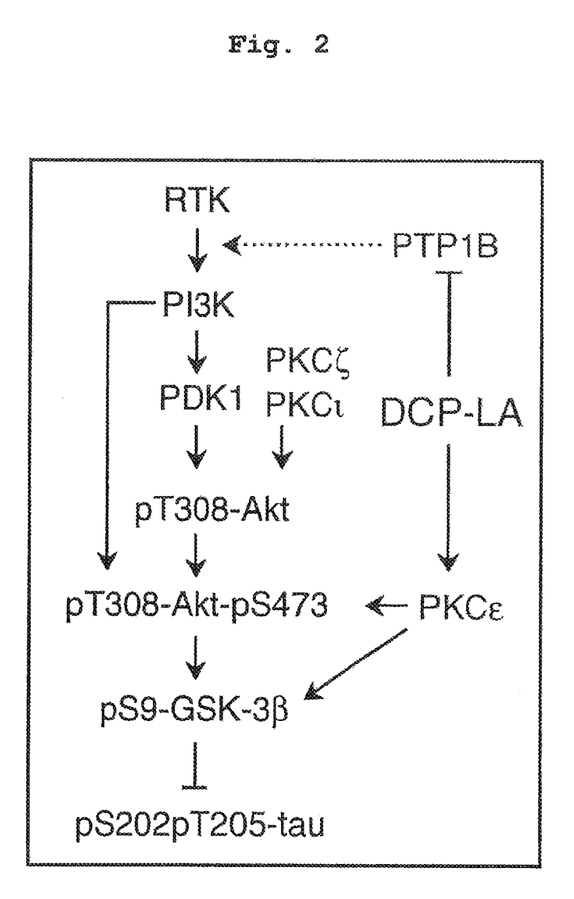
FIG. 2 depicts the pathway showing that DCP-LA inhibits PTP1B to indirectly activate tyrosine kinase and activate Akt, or DCP-LA activates PKCε, activated PKCε directly phosphorylates and activates Akt to phosphorylate and inactivate GSK-3β, whereby phosphorylation of τ protein is suppressed. In addition, it depicts the pathway showing that DCP-LA activates PKCε, and activated PKCε phosphorylates and inactivates GSK-3β, whereby phosphorylation of τ protein is suppressed.

The results show that DCP-LA inhibits PTP1B in a concentration-dependent manner. This further suggests that DCP-LA indirectly activates receptor tyrosine kinase (RTK) and is involved in Akt activation pathway (reference pathway is shown in FIG. 2).

Example 2

Akt Activating Action, GSK-3β Phosphorylation Promoting Action and Suppressive Action on τ Protein Phosphorylation Induced by $A\beta_{1-42}$ (Material and Method)

A rat hippocampus section (male Wister rat, 6-week-old, 400 μm) was incubated in an artificial cerebrospinal fluid (117 mM NaCl, 3.6 mM KCl, 1.2 mM $NaH_2PO_4$, 1.2 mM $MgCl_2$, 2.5 mM $CaCl_2$, 25 mM $NaHCO_3$, and 11.5 mM glucose) oxygenated with 95% $O_2$ and 5% $CO_2$, in the presence or absence of DCP-LA (100 nM) at 34° C. for 3 min. In another experiment set, the section was incubated with $A\beta_{1-42}$ (1 μM) for 3 hr in the presence or absence of DCP-LA (100 nM). After incubation, the section was homogenized by sonication in an ice-cooled cell lysis buffer containing 1% (v/v) protease inhibitor cocktail and 1% (v/v) phosphatase inhibitor cocktail, and the homogenate was centrifuged (3,000 rpm, 5 min, 4° C.). The protein concentration of the supernatant was measured using BCA protein assay kit (Thermo Fisher Scientific, Rockford, Ill., USA). The protein was separated by SDS-polyacrylamide gel electrophoresis (SDS-PAGE), and transferred onto polyvinylidene difluoride membranes.

The blotting membranes were blocked with TBS-T [150 mM NaCl, 0.1% (v/v) Tween20 and 20 mM Tris, pH 7.5] containing 5% (w/v) BSA, and sequentially reacted with each of the following antibodies.

Anti-phospho-Akt (Thr308) antibody (Cell Signaling Technology, Inc., Danvers, Mass., USA)

Anti-phospho-Akt (Ser473) antibody (Cell Signaling Technology, Inc., Danvers, Mass., USA)

Anti-Akt antibody (Cell Signaling Technology, Inc., Danvers, Mass., USA)

Anti-phospho-GSK-3β (Ser9) antibody (Cell Signaling Technology, Inc., Danvers, Mass., USA)
Anti-GSK-3β antibody (Cell Signaling Technology, Inc., Danvers, Mass., USA)
Anti-phospho-Tau (Ser202/Thr205) antibody (Thermo Fisher Scientific)
Anti-Tau antibody (Cell Signaling Technology, Inc., Danvers, Mass., USA)

After washing, the membranes were reacted with horseradish peroxidase-conjugated goat anti-mouse IgG antibody or goat anti-rabbit IgG antibody. The immunoreactivity was detected using ECL kit (GE Healthcare, Piscataway, N.J., USA), and visualized using a chemical luminescence detection system (chemiluminescence detection system; GE Healthcare).
(Results)

Figure 3:
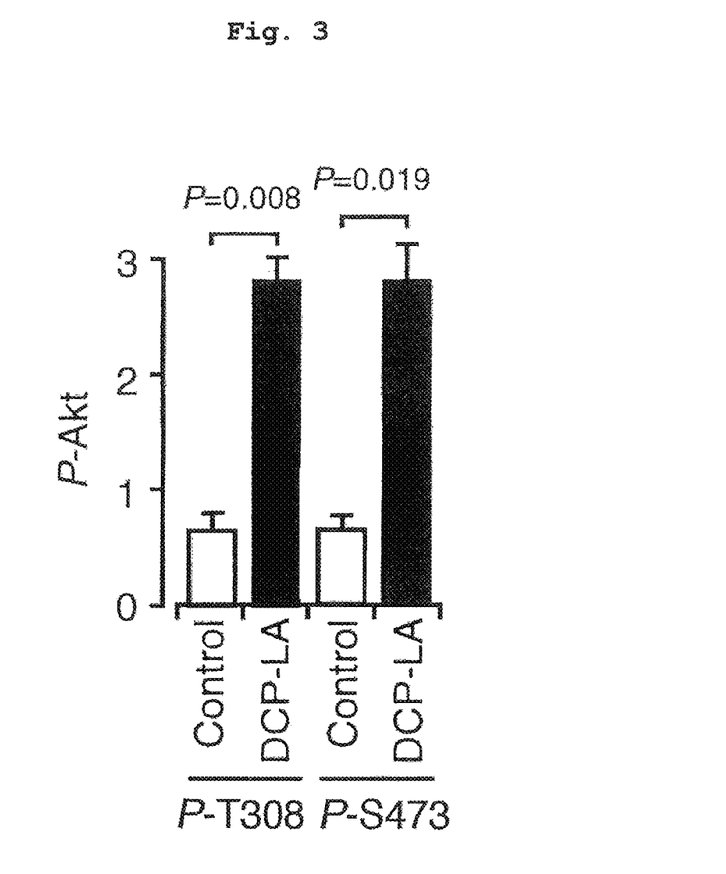

The study results of Akt activation are shown in FIG. 3. The results show that DCP-LA has an action to activate Akt (Akt is activated by phosphorylation of Thr308 and Ser473).

Figure 4:
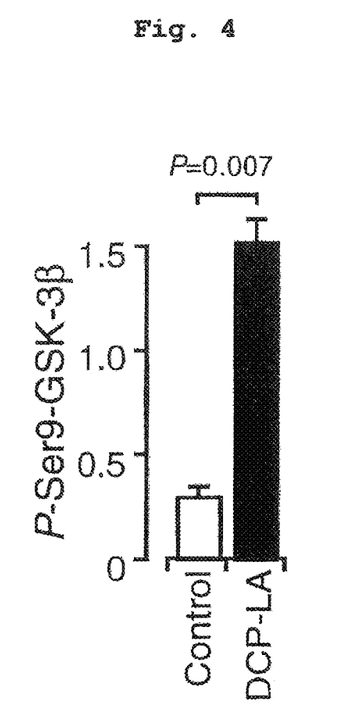

The study results of phosphorylation of GSK-3β are shown in FIG. 4. The results show that DCP-LA phosphorylates (inactivates) GSK-3β.

Figure 5:
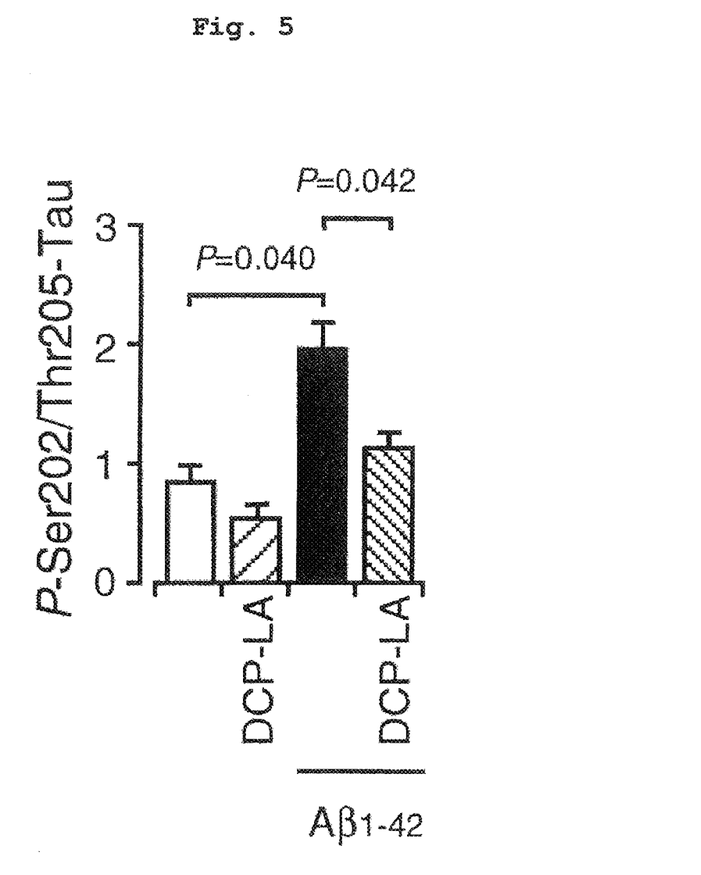

The study results of phosphorylation of τ protein induced by $Aβ_{1-42}$ are shown in FIG. 5. The results show that DCP-LA suppresses phosphorylation of τ protein induced by $Aβ_{1-42}$. In other words, they suggest that DCP-LA suppresses formation of neurofibrillary tangle (NFT).

Example 3

Acquisition Latency and Retention Latency-Improving Effect (Material and Method)

XFAD transgenic mouse is an animal model of Alzheimer's disease (AD), and contains five mutations of familial Alzheimer's disease (FAD) [Swedish, Florida and London mutations of human amyloid precursor protein (APP), and M146L and L286V mutations of presenilin (PS); Oakley H et al., J. Neurosci. 2006; 26: 10129-10140]. In 5XFAD mouse, Swedish mutation increases production of total amyloid β peptide (Aβ), and the remaining mutations particularly promote production of $Aβ_{1-42}$.

All handling of the animals were approved by the Hyogo College of Medicine Animal Experiment Committee, and performed according to the guideline relating to the management and use of experiment animals of NIH (National Institute of Health).

5XFAD mouse was purchased from The Jackson Laboratory (Bar Harbor, Me., USA), and maintained by crossing with heterozygous transgenic mouse with B6/SJLF1 breeding stock. Non-transgenic wild-type litter-mate was used as a control. All experiments were performed at the age of 5.5-6.5 months.

A circular plastic water tank (diameter 90 cm, depth 36 cm) was used. The inside of the water tank was completely painted in white, and water containing White India ink was filled up to 20 cm from the bottom (22-25° C.). A platform (diameter 11 cm) painted in white was placed in water such that it was 1 cm below the water surface. The water tank was placed in a test room, and several marks seen by the mouse from the water tank were put thereon. During the test, the position of the marks was not changed. A platform was placed a predetermined position from the equal distance from the center and the end of the water tank, namely, center of one quadrant. At one of the randomly selected 3 points, the mouse was released facing the wall of the water tank, and the time necessary for evacuating on the platform (acquisition latency) was measured. When smoothly evacuated, the mouse was left on the platform for 10 seconds. When the mouse failed to find the platform within 90 seconds, the test was stopped and the mouse was placed on the platform for 10 seconds. The test was performed twice a day, and the second test was started at 30 seconds after the first test. The test was continuously performed for 8 days, and the mean (±SEM) of acquisition latency of continuous 2 days until the mouse reached the platform was calculated. After 7 days, the platform was removed and the time necessary for reaching the place where the platform was located (retention latency) was measured.

DCP-LA and galanthamine were dissolved in polyethylene glycol (PEG). DCP-LA, galanthamine and PEG were administered with an oral gavage needle 30 min before the water maze test.
(Results)

Figure 6:
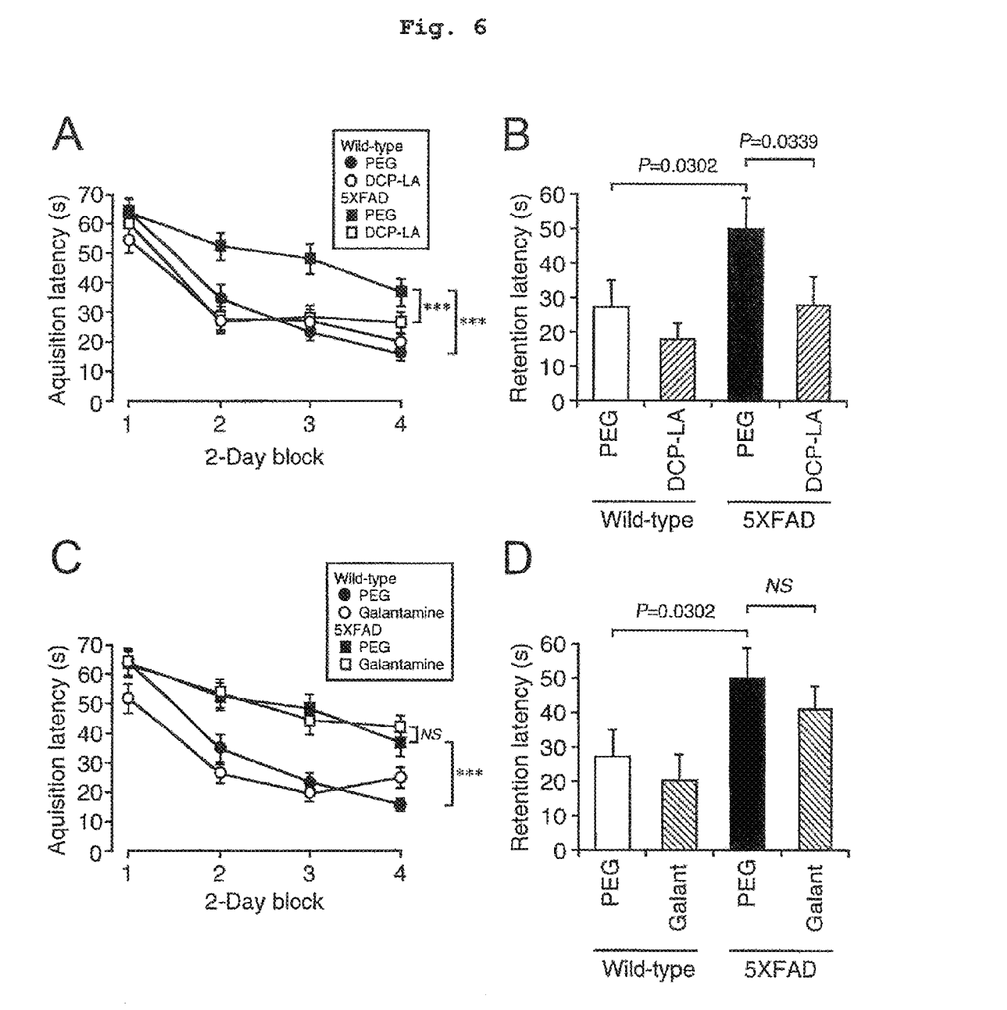

The results are shown in FIG. 6. The acquisition latency and retention latency were significantly extended in 5XFAD mouse as compared to wild-type mouse. DCP-LA improved extension of both latencies to nearly normal levels. In contrast, galanthamine showed no effect. The results show that DCP-LA is an effective medicine that improves Alzheimer-type dementia.

Example 4

GSK-3β Phosphorylation Promoting Action (Material and Method)
GSK-3β Assay Under Cell-free Conditions Human recombinant GSK-3β (Sigma, St. Louis, Mo., USA) was reacted with His-tagged human recombinant PKCε (Calbiochem, San Diego, Calif., USA) under cell-free conditions in the presence or absence of a given concentration (1-100 μM) of DCP-LA, and with or without addition of GF109203X, in a culture medium containing 20 mM Tris-HCl (pH 7.5), 5 mM Mg-acetate, 12.5 mM glycerol 2-phosphate and 250 μM ATP at 30° C. for 20 min. The protein was separated by SDS-polyacrylamide gel electrophoresis (SDS-PAGE), and transferred on a polyvinylidene difluoride membrane. The blotting membrane was blocked with TBS-T [150 mM NaCl, 0.1% (v/v) Tween20 and 20 mM Tris, pH 7.5] containing 5% (w/v) BSA, and sequentially reacted with anti-serine 9 phosphorylated GSK-3β antibody (Cell Signaling Technology, Inc., Danvers, Mass., USA) or anti-GSK-3β antibody (Cell Signaling Technology, Inc., Danvers, Mass., USA). After washing, the membrane was reacted with horseradish peroxidase conjugated goat anti-mouse IgG antibody or goat anti-rabbit IgG antibody. The immunoreactivity was detected using ECL kit (GE Healthcare, Piscataway, N.J., USA), and visualized using a chemical luminescence detection system (chemiluminescence detection system; GE Healthcare).
(Results)

Figure 7:
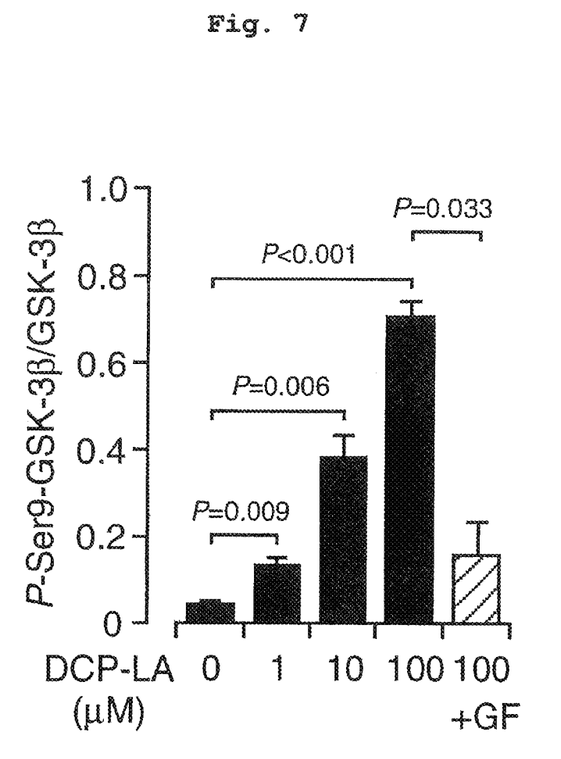

The results are shown in FIG. 7. The results show that DCP-LA phosphorylates (inactivates) GSK-3β in the presence of PKCε. Since phosphorylation is suppressed by GF109203X (PKC inhibitor), it is clearly PKCε dependent.

INDUSTRIAL APPLICABILITY

DCP-LA has a protein tyrosine phosphatase 1B (PTP1B) inhibitory action, an Akt activating action, a GSK-3β phosphorylation promoting action, and a suppressive action on τ protein phosphorylation induced by $Aβ_{1-42}$, and is useful as a therapeutic drug for Alzheimer-type dementia, an antidepressant and/or an anti-aging drug. Based on such pharmacological actions, it is also useful as various reagents for study, and the reagent becomes a promising tool for the development of a novel therapeutic drug for dementia, an antidepressant, or an anti-aging drug.

This application is based on a patent application No. 2013-033668 filed in Japan (filing date: Feb. 22, 2013), the contents of which are incorporated in full herein.

The invention claimed is:

1. A method of activating Akt comprising administering an effective amount of DCP-LA to a patient in need thereof, wherein the DCP-LA activates PKCε, and the PKCε directly activates Akt in the patient.

2. A method of suppressing GSK-3β comprising administering an effective amount of DCP-LA to a patient in need thereof, wherein the DCP-LA activates PKCε, and the PKCε directly suppresses GSK-3β in the patient.

* * * * *